United States Patent [19]

Padawer

[11] Patent Number: 4,463,263
[45] Date of Patent: Jul. 31, 1984

[54] POSITRON-ANNIHILATION-RADIATION TRANSMISSION GAUGE

[75] Inventor: Gerald M. Padawer, East Hills, N.Y.

[73] Assignee: Grumman Aerospace Corporation, Bethpage, N.Y.

[21] Appl. No.: 307,279

[22] Filed: Sep. 30, 1981

[51] Int. Cl.³ .................... G01T 1/20; G01N 23/00
[52] U.S. Cl. ....................... 250/363 R; 250/308; 250/358.1
[58] Field of Search ............... 250/307, 308, 358.1, 250/359.1, 360.1, 363 R, 363 S, 366, 369; 376/258

[56] References Cited

U.S. PATENT DOCUMENTS

| | | | |
|---|---|---|---|
| 2,613,326 | 10/1952 | Herzog . | |
| 2,903,590 | 9/1959 | Somerville | 250/308 |
| 2,968,729 | 1/1961 | Pepper et al. | 250/308 |
| 3,011,057 | 11/1961 | Anger | 250/363 S |
| 3,193,680 | 7/1965 | Anderson | 250/307 |
| 3,234,386 | 2/1966 | Leventhal et al. . | |
| 3,573,458 | 4/1971 | Anger . | |
| 3,593,025 | 7/1971 | Grosskreutz | 250/358 |
| 3,668,386 | 6/1972 | Blecherman | 250/307 |
| 3,786,256 | 1/1974 | Untermyer | 250/363 R |
| 3,970,855 | 7/1976 | Holt et al. | 250/358 |
| 3,980,885 | 9/1976 | Steward et al. | 250/307 |
| 4,064,438 | 12/1977 | Alex et al. | 250/308 |
| 4,194,115 | 3/1980 | Whitehead et al. | 250/308 |
| 4,268,753 | 5/1981 | Murakami et al. | 250/357.1 |

Primary Examiner—Janice A. Howell
Attorney, Agent, or Firm—Morgan, Finnegan, Pine, Foley & Lee

[57] ABSTRACT

A radiographic method and apparatus for nondestructively monitoring a specimen for density variations are disclosed.

A positron-annihilation-radiation-emitting point source is situated approximately midway along the axis separating two detectors sensitive to positron-annihilation (0.511-MeV photon) radiation. The outputs of the two detectors are fed to an electronic circuit that reckons only time-coincident events that are sensed simultaneously in the two detectors. The specimen to be measured is positioned between the source and one of the detectors such that the cone of detected, i.e., coincident, photons intercepts the region of interest. The number of coincidences that are counted in a preset time interval are recorded, or, alternatively, the coincidence count rate is monitored directly with a ratemeter.

A linear scan of the region of interest is performed by the sequential displacing of the source/detectors axis with respect to the measured specimen, or the specimen with respect to the source/detectors axis. The number of coincidence counts accumulated within a preset time interval are recorded for each displacement. The spatial variation of density within the specimen is inferred from corresponding variations in the coincidence count rate.

8 Claims, 4 Drawing Figures

POSITRON-ANNIHILATION-RADIATION TRANSMISSION GAUGE

BACKGROUND OF THE INVENTION

The present invention relates to a method and apparatus for non-destructively monitoring a specimen for density variations. More specifically, it relates to the application of certain phenomena and principles of gamma-ray-transmission techniques to the generating, detecting, and interpreting of positron-annihilation-radiation incident upon, and interacting with, and attenuated by the interrogated specimen.

In many applications, it is necessary to discern the presence of adjacent materials of differing densities, otherwise obscured from view. For example, it may be desirable to detect the presence within an opaque vessel or structure, of heavy fluids, such as water, oil, liquid metals, etc., located in cavities, channels, voids, or galleries normally invisible, or otherwise inaccessible, to probes.

A specific example of such an application deals with the maintenance and reliability of aircraft. It is well known that dynamic balance of an aircraft propellor must be achieved in order that vibration problems might minimized. Quite often, if vibrations are sensed in an aircraft, and if propellor imbalance is deemed blameworthy, the propellors must be removed and disassembled in order that the reason(s) for propellor-blade imbalance might be learned. In such instances, oil from the pitch-control mechanism located in the propellor hub might be found to have infiltrated the plugged cavity in the blade shank, causing imbalance. Such examinations are time-consuming, at best, when invasive oil is indeed found, and are particularly wasteful of time in those cases in which the cavity proves to be empty.

The utilization of conventional X-ray radiography techniques to sense the presence of oil in the blade cavity has several drawbacks. In particular, it requires expensive x-ray equipment, configured specifically for the intended application, which would have to be located at each installation where at the aircraft are based. Moreover, specially-trained personnel are required to operate and maintain X-ray equipment. And, finally, monitoring, by radiation-safety personnel, of the X-ray equipment might be inconvenient, as well as impractical.

An optimal densitometer would have several basic capabilities. First, it should not present a health hazard to personnel utilizing the device. It should utilize a readily available, encapsulated, long-lived radioactive positron-emitting source, its strength not exceeding ten microCuries, thereby obviating radiation hazard, and eliminating, hence, the need for licensing the source, or parts of the apparatus, or its application procedures.

Second, it should be versatile and reliable. It should be portable to accommodate measurements "in the field", exhibit a high degree of spatial resolution, and operate over a wide dynamic range.

And, finally, it should be relatively insensitive to normal levels of environmental background radiation.

It is believed that prior to the present invention, there has not been available, conforming with the constraints and meeting the requirements cited above, a method and apparatus for nondestructively measuring the spatial variation of density within an opaque vessel or structure. Thus, the need for such a system had heretofore gone unfulfilled.

It is accordingly a general object of the present invention to overcome the aforementioned limitations and drawbacks associated with conventional densitometers, and to fulfill the needs mentioned, by providing a method and apparatus for sample density monitoring having all of the desirable attributes noted above.

It is a particular object of the invention to provide a radiographic method and apparatus for nondestructively monitoring a specimen for density variations.

It is a further object of the invention to provide a method and apparatus predicated upon positron-annihilation-radiation interactions for nondestructively ascertaining abrupt, as well as gradual, spatial variation of density within a specimen.

Other objects will be apparent in the following detailed description, and in the practice of the invention.

SUMMARY OF THE INVENTION

The foregoing and other objects and advantages which will be apparent in the following detailed description of the preferred embodiment, or in the practice of the invention, are achieved by the invention disclosed herein, which generally may be characterized as a method and apparatus for nondestructively ascertaining the spatial variation of density within a specimen, the method comprising the steps of: situating said specimen between a positron-annihilation-radiation-emitting source, and one of a pair of photon-sensitive detectors, said source being located approximately midway along the axis separating said pair of detectors; reckoning only time-coincident events sensed simultaneously in both of the detectors; recording the number of coincidences counted in a preset time interval or, alternatively, monitoring directly the coincidence count rate; and ascertaining the spatial variation of density from corresponding variations in the recorded data; and the apparatus comprising: means for situating said specimen between a positron-annihilation-radiation-emitting source and one of a pair of photon-sensitive detectors, said source being located approximately midway along the axis separating said pair of detectors; means for reckoning only time-coincident events sensed simultaneously in both of the detectors; and means for recording the number of coincidences counted in a preset time interval, or, alternatively, means for monitoring directly the coincidence count rate.

BRIEF DESCRIPTION OF THE DRAWINGS

Serving to illustrate an exemplary embodiment of the present invention are the drawings of which.

DETAILED DESCRIPTION OF THE PREFERRED EMBODIMENT

Figure 1:
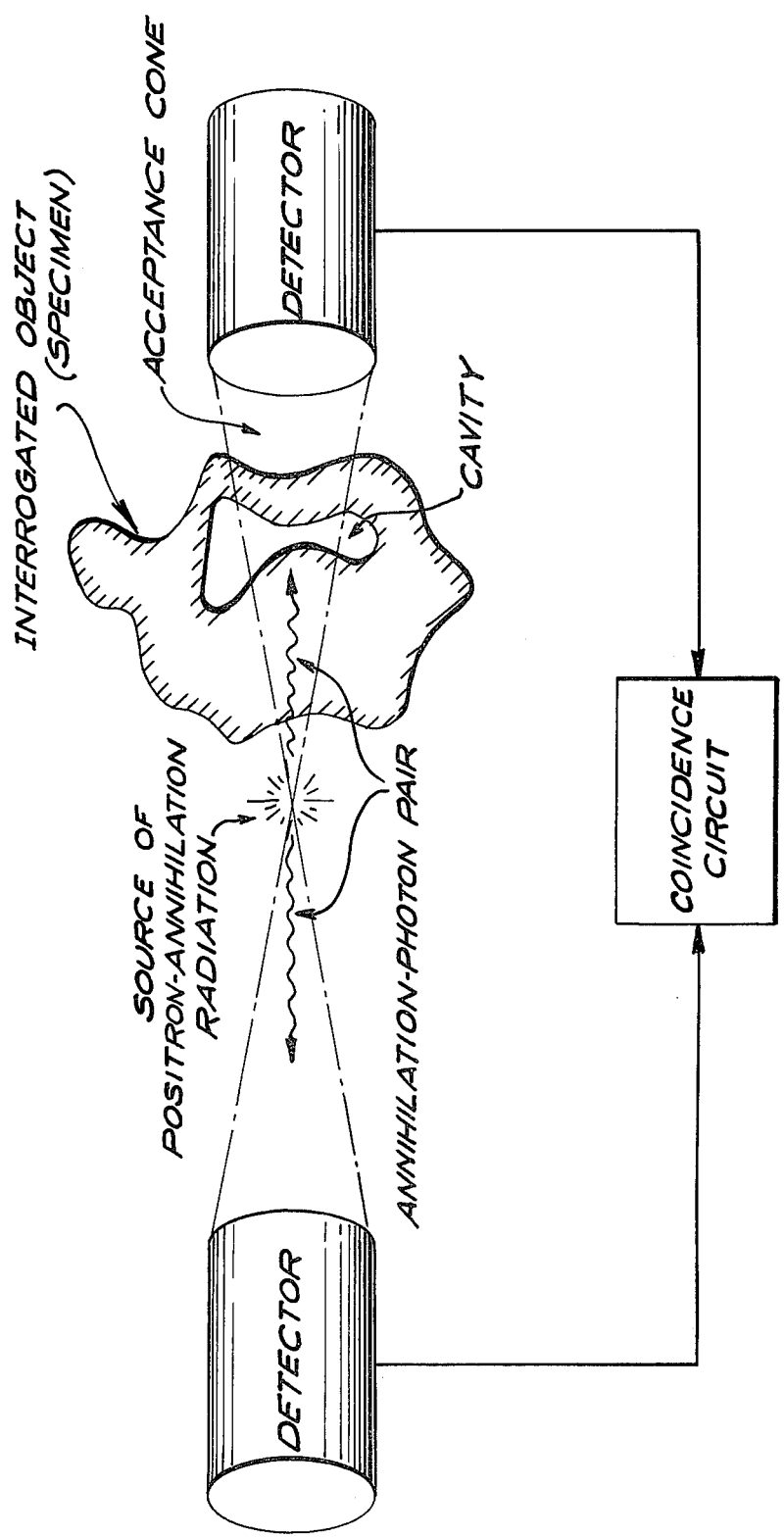
FIG. 1 illustrates the principles of operation of a positron-annihilation-radiation transmission gauge, in accordance with the present invention.

The present invention is based on the use of a positron-annihilation-radiation-emitting point source, for example, encapsulated sodium-22, and two time-coincident NaI(T1) detectors arrayed in a collinear configuration as illustrated in FIG. 1. As shown therein, the source and the diametrically opposed detectors are aligned on a common axis such that the detector faces are substantially equidistant from the source. Each emitted positron, on stopping in the source matrix, mutually annihilates with an electron, creating a pair of photons, each having an energy equal to the rest-energy of an electron, i.e., 0.511-MeV, the annihilation photons being emitted in mutually opposed directions.

If the outputs of the detectors are presented to an electronic coincidence circuit that responds only to pulses generated simultaneously in both, only those events corresponding to the detection of annihilation-photon pairs emitted in the geometric cones subtended in common by the detectors will be reckoned. The likelihood of chance coincidences is small, provided the resolving time of the electronic circuit is small, and provided the count rate in each detector is sufficiently low. Both these conditions are met by the present invention.

Figure 2:
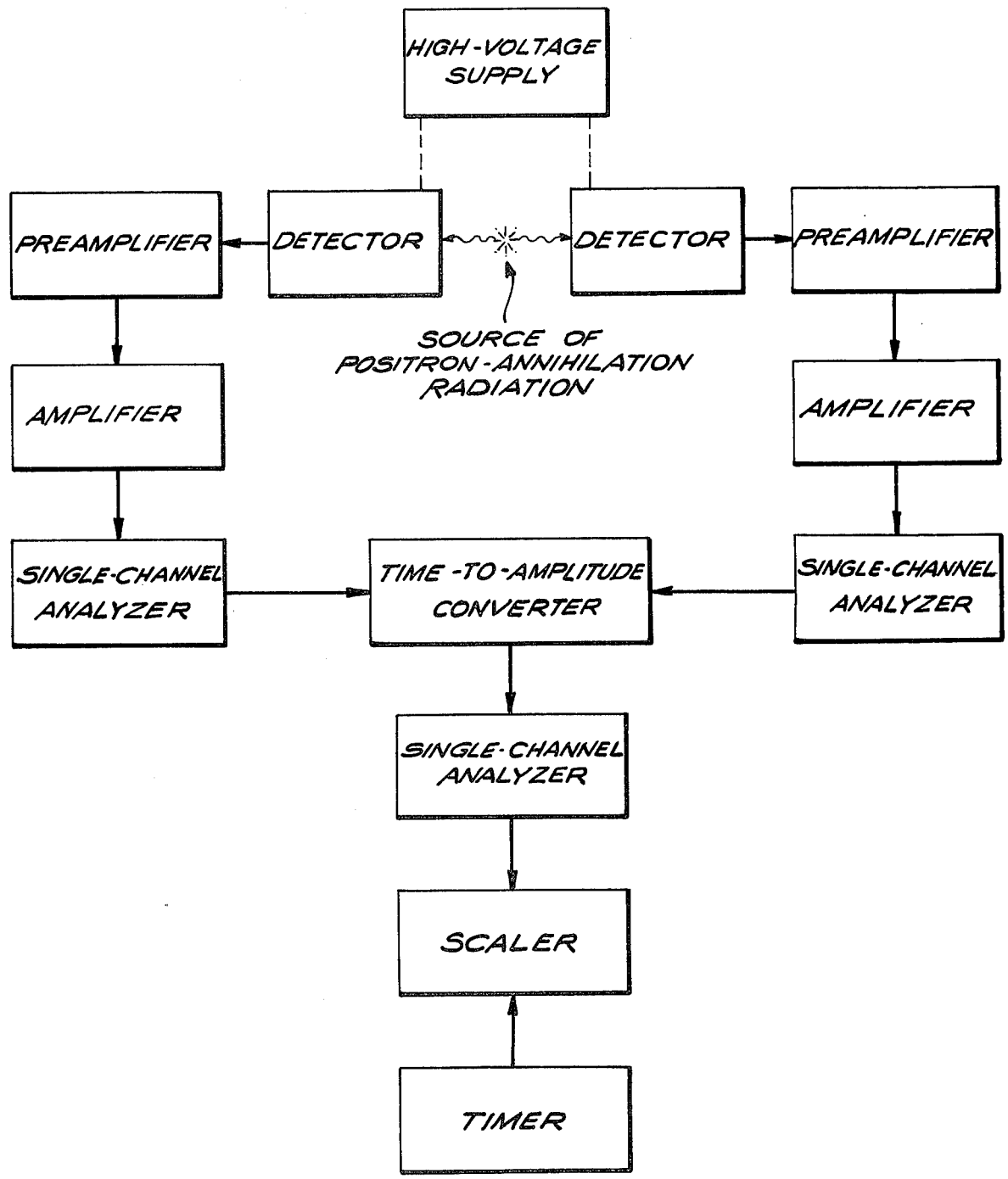
FIG. 2 is a block diagram of the coincidence circuit electronics of a positron-annihilation-radiation transmission gauge, in accordance with the present invention.

Referring now to FIG. 2, a block diagram of the coincidence circuit electronics of a positron-annihilation-radiation transmission gauge, in accordance with the present invention, is illustrated. As shown therein, a source of positron-annihilation radiation, such as encapsulated sodium-22, is located approximately equidistant between a pair of detectors sensitive to 0.511-MeV photon radiation. A direct-current high-voltage power supply is used to provide voltage to each of the detectors. The output of each of the photon-sensitive detectors is fed to a corresponding preamplifier-amplifier stage. The amplified bipolar outputs are presented to a corresponding pair of single-channel analyzers, each of which generates a narrow timing marker in phase with the zero-crossover of the respective bipolar pulse. The single-channel-analyzer outputs are fed to a time-to-amplitude converter which generates a pulse, the amplitude of which is directly proportional to the difference in times of arrival between the two single-channel-analyzer timing-marker output pulses. The output of the time-to-amplitude converter is fed to a single-channel analyzer, the lower and upper discriminator levels of which constitute a "window" that passes only those time-to-amplitude-converter output signals that correspond to coincident events. The output of the single-channel analyzer is connected to a ratemeter, or, alternatively, to a scaler, which tallies the number of coincidences in a preset time interval. A timer activates the scaler for the predetermined time period.

In utilizing the teachings of the present invention, the specimen to be measured is positioned between the positron-annihilation-radiation-emitting source and one of the photon-sensitive detectors, such that the cone of detected, i.e., coincident, photons intercepts the region of interest. The number of coincidences that are tallied in a preset time interval are recorded. A linear scan of the region of interest is performed by the sequential displacing of the source/detectors axis with respect to the interrogated specimen, or the specimen with respect to the source/detectors axis. The number of coincidence counts are recorded for each displacement. The spatial variation of density within the specimen, including, in particular, the locating within the specimen of interfaces separating adjacent materials of abruptly differing densities is inferred from corresponding variations and/or discontinuities in the recorded data plot.

It is noted that the unique delta-function property of the angular correlation of the two-photon positron-annihilation process, i.e., the special attribute by which photon pairs are simultaneously emitted in precisely mutually opposite directions, further enhances the efficiency of the system by not requiring that the windows of the single-channel analyzers in the detector circuits restrict the acceptable pulse-height range to that corresponding to the full energy of the positron-annihilation radiation; the well-populated low-energy component of the (mutually coincident) pulse-height distributions comprises mostly the Compton-scattering response of the detectors to photons unscattered by the interposed object, or minimally scattered by it through very small angles; the geometric limitation as well as the pulse-simultaneity constraint significantly thwart the registering of photons scattered through larger angles.

Moreover, it is noted that the attainable spatial resolution, defined by the angle(s) subtended by the detector(s), improves with increasing separation between the detectors; but count-rate reduction is the consequent penalty. As a spatial scan of the interrogated object is performed, fluctuations in the coincidence count rate reflect variations in its density.

Figure 3:
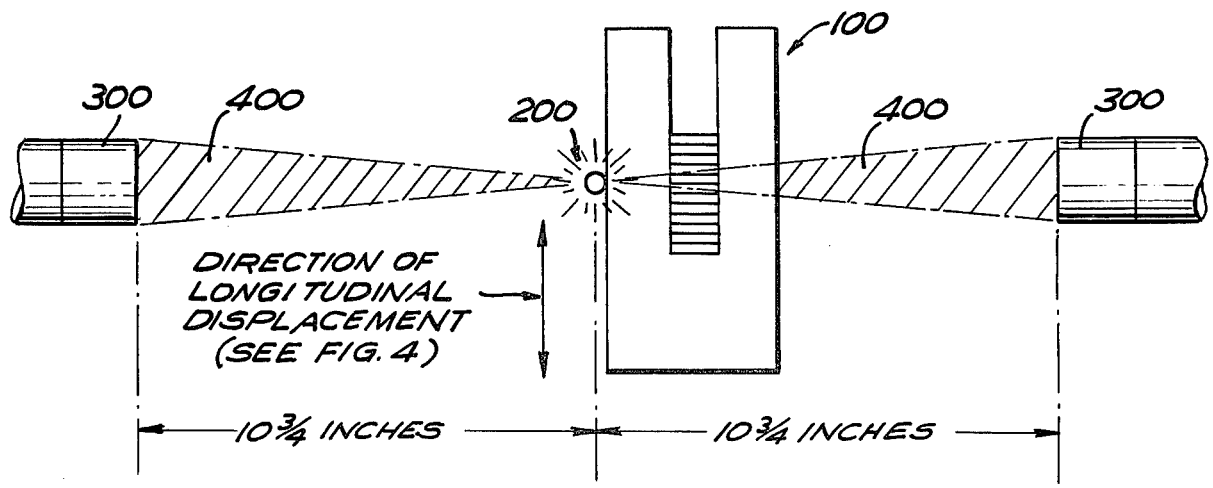
FIG. 3 is a schematic illustration of the geometry of a positron-annihilation-radiation transmission gauge.

Referring now to FIG. 3, the geometry of one type of positron-annihilation-radiation transmission guage, in accordance with the teachings of the present invention, is illustrated. As shown therein, a specimen, 100, consisting of seven-and-one-half-inch-high, four-inch-diameter solid aluminum cylinder, having a five-inch-long, one-inch-diameter hole with a two-and-one-half-inch-high column of oil therein is situated one-quarter inch from a 6.4-microCurie positron-annihilation-radiation-emitter (encapsulated sodium-22) source, 200. The source, 200, is situated midway along the line-of-sight separating a pair of detectors, 300, each consisting of a two-inch-diameter, two-inch-height thallium-activated sodium-iodide scintillator coupled to a photomultiplier tube. The spacing between the source, 200, and each of the detectors, 300, is ten-and-three-quarter inches. Shaded area, 400, depicts the cone to which the detected photons are restricted.

Figure 4:
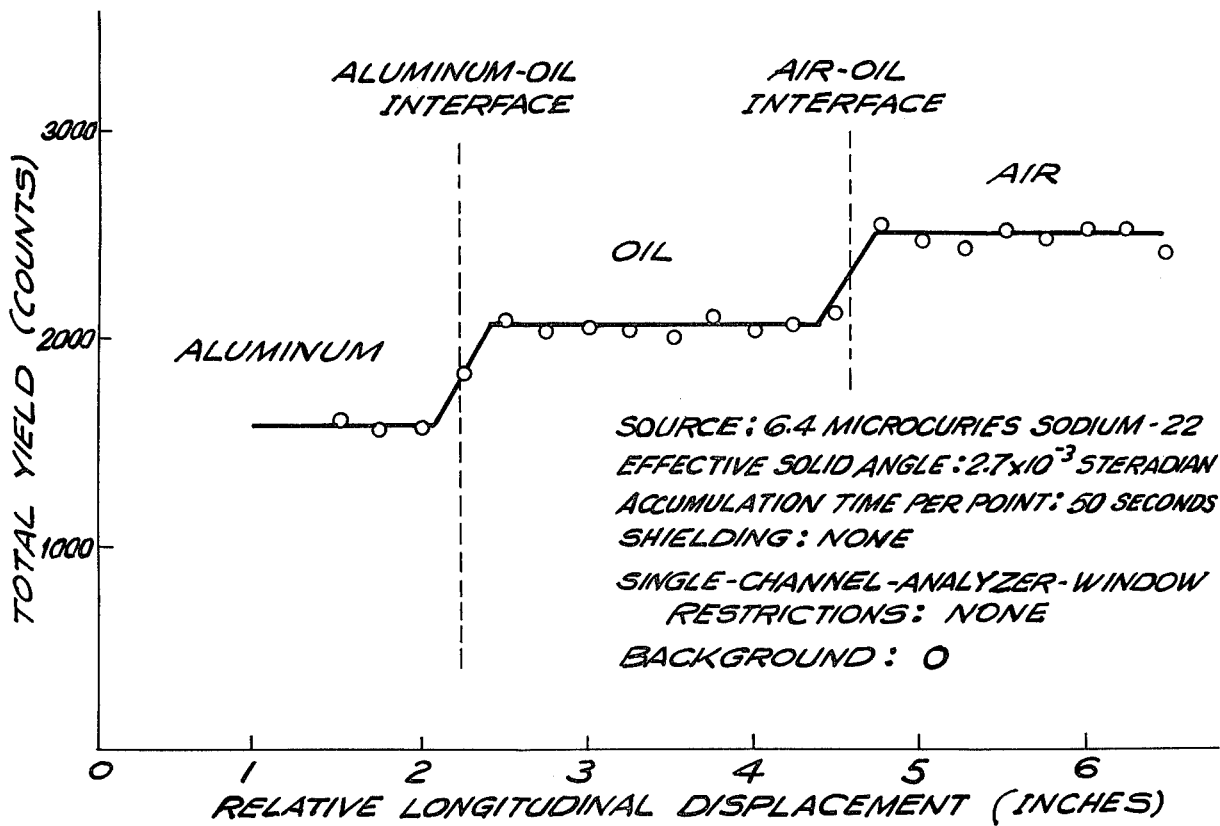
FIG. 4 illustrates the results obtained with the apparatus illustrated in FIG. 3.

FIG. 4 illustrates the plot of total yield versus relative longitudinal displacement which was obtained with the positron-annihilation-radiation transmission gauge configuration illustrated in FIG. 3. As shown therein, the discontinuity in the recorded data plot in the relative longitudinal displacement region of two to four-and-one-half inches is indicative of the two-and-one-half-inch-high column of oil located within the solid aluminum cylinder.

It has thus been shown that the present invention provides a method and apparatus for nondestructively ascertaining the location within a specimen of an interface separating adjacent materials of differing densities. By a logical extension of the result of the above experiment which demonstrates the discernibility of abrupt interfaces, gradual spatial variations of density can be measured as well.

Although one particular embodiment of the invention has been illustrated and described, modifications thereof will become apparent to those skilled in the art. It is seen to have utility in intense radiation environments, wherein conventional gamma-ray transmission of X-ray radiographic techniques would be compromised by the ambient radiation field. Thus, for example, it can measure the level of a fluid contained within a sealed opaque vessel inside a nuclear-reactor containment structure. Moreover, it can perform densitometry, not only of non-radioactive objects, but, as well, of radioactive objects which heretofore have defied radiographic interrogation because of the intensity of radiation emanating therefrom.

Accordingly, it is clear that the above description of the preferred embodiment in no way limits the scope of the present invention which is defined by the following claims.

What is claimed is:

1. A method for nondestructively ascertaining the spatial variation of density within a specimen comprising the steps of:
    (a) situating said specimen between a positron-annihilation radiation-emitting source, in which a positron annihilates with an electron to create a pair of photons, and one of a pair of photon-sensitive detectors, said source being located approximately midway along the line-of-sight separating said pair of detectors which are each responsive to one of the photons;
    (b) reckoning only time-coincident events sensed simultaneously in both of the detectors;
    (c) recording the number of coincidences counted in a preset time interval; and
    (d) ascertaining the spatial variation of density from corresponding variations in the recorded data.

2. A method for nondestructively ascertaining the spatial variation of density within a specimen comprising the steps of:
    (a) situating said specimen between a positron-annihilation radiation-emitting source, in which a positron annihilates with an electron to create a pair of photons, and one of a pair of photon-sensitive detectors, said source being located approximately midway along the line-of-sight separating said pair of detectors which are each responsive to one of the photons;
    (b) reckoning only time-coincident events sensed simultaneously in both of the detectors;
    (c) monitoring the coincidence count rate; and
    (d) ascertaining the spatial variation of density from corresponding variations in the monitored data.

3. A method for nondestructively ascertaining the spatial variation of density within a specimen comprising the steps of:
    (a) situating said specimen between a positron-annihilation-radiation-emitting source, in which a positron annihilates with an electron to create a pair of photons, and one of a pair photon-sensitive detectors, said source being located approximately midway along the axis separating said pair of detectors which are each responsive to one of the photons;
    (b) reckoning only time-coincident events sensed simultaneously in both of the detectors;
    (c) recording the number of coincidences counted in a preset time interval;
    (d) displacing said detectors' common axis with respect to said specimen and repeating steps (b) and (c) above; and
    (e) ascertaining the spatial variation of density from corresponding variations in the recorded data.

4. A method for nondestructively ascertaining the spatial variation of density within a specimen comprising the steps of:
    (a) situating said specimen between a positron-annihilation-radiation-emitting source, in which a positron annihilates with an electron to create a pair of photons, and one of a pair of photon-sensitive detectors, said source being located approximately midway along the axis separating said pair of detectors which are each responsive to one of the photons;
    (b) reckoning only time-coincident events sensed simultaneously in both of the detectors;
    (c) monitoring the coincidence count rate;
    (d) displacing said detectors' common axis with respect to said specimen and repeating steps (b) and (c) above; and
    (e) ascertaining the spatial variation of density from corresponding variations in the monitored data.

5. A method for nondestructively ascertaining the spatial variation of density within a specimen comprising the steps of:
    (a) situating said specimen between a positron-annihilation-radiation-emitting source, in which a positron annihilates with an electron to create a pair of photons, and one of a pair of photon-sensitive detectors, said source being located approximately midway along the axis separating said pair of detectors which are each responsive to one of the photons;
    (b) reckoning only time-coincident events sensed simultaneously in both of the detectors;
    (c) recording the number of coincidences counted in a preset time interval;
    (d) displacing said specimen with respect to said detectors' common axis and repeating steps (b) and (c) above; and
    (e) ascertaining the spatial variation of density from corresponding variations in the recorded data.

6. A method for nondestructively ascertaining the spatial variation of density within a specimen comprising the steps of:
    (a) situating said specimen between a positron-annihilation-radiation-emitting source, in which a positron annihilates with an electron to create a pair of photons, and one of a pair of photon-sensitive detectors, said source being located approximately midway along the axis separating said pair of detectors which are each responsive to one of the photons;
    (b) reckoning only time-coincident events sensed simultaneously in both of the detectors;
    (c) monitoring the coincidence count rate;
    (d) displacing said specimen with respect to said detectors' common axis and repeating steps (b) and (c) above; and
    (e) ascertaining the spatial variation of density from corresponding variations in the monitored data.

7. Apparatus for nondestructively ascertaining the spatial variation of density within a specimen comprising:
    (a) means for situating said specimen between a positron-annihilation-radiation-emitting source, in which a positron annihilates with an electron to create a pair of photons, and one of a pair of detectors, said source being located approximately midway along the axis separating said pair of detectors which are each responsive to one of the photons;

(b) means for reckoning only time-coincident events sensed simultaneously in both of the detectors; and
(c) means for recording the number of coincidences counted in a preset time interval.

8. Apparatus for nondestructively ascertaining the spatial variation of density within a specimen comprising:
(a) means for situating said specimen between a positron-annihilation-radiation-emitting source, in which a positron annihilates with an electron to create a pair of photons, and one of a pair of detectors, said source being located approximately midway along the axis separating said pair of detectors which are each responsive to one of the photons;
(b) means for reckoning only time-coincident events sensed simultaneously in both of the detectors; and
(c) means for monitoring the coincidence count rate.

* * * * *